United States Patent [19]

Cryer

[11] Patent Number: 4,886,671
[45] Date of Patent: Dec. 12, 1989

[54] METHOD OF COMBATING DUTCH ELM DISEASE

[76] Inventor: John Cryer, 4305 S. Atlantic Ave., New Smyrna Beach, Fla. 32069

[21] Appl. No.: 664,560

[22] Filed: Oct. 25, 1984

Related U.S. Application Data

[63] Continuation-in-part of Ser. No. 442,529, Nov. 18, 1982, abandoned.

[51] Int. Cl.$^4$ ................... A01N 55/02; A01N 59/16
[52] U.S. Cl. ........................... 424/641; 514/494; 514/936
[58] Field of Search .............. 424/145, 289, 641; 514/936, 494

[56] References Cited

U.S. PATENT DOCUMENTS

| | | | |
|---|---|---|---|
| 3,551,554 | 12/1970 | Herschler | 424/7 |
| 3,756,801 | 9/1973 | Herschler | |
| 4,335,109 | 6/1982 | Hill | 424/145 |

OTHER PUBLICATIONS

Keil; *Agricultural Chemicals*, "DMSO Shows Great Promise as Carrier of Agricultural Toxicants", Apr., 1965; pp. 23, 24 & 128.

*Primary Examiner*—Allen J. Robinson
*Attorney, Agent, or Firm*—Michael G. Berkman

[57] ABSTRACT

Dutch elm disease is counteracted by injecting elm trees susceptible to, or having such disease, with a composition comprising a water soluble zinc salt dissolved in water and mixed with dimethyl sulfoxide in certain predetermined proportions, preferably applied at a time when the sap is returning to the root system.

6 Claims, No Drawings

METHOD OF COMBATING DUTCH ELM DISEASE

BACKGROUND

Dutch elm disease is a scourge that has destroyed many millions of elm trees in the United States of America, in The Dominion of Canada, in Great Britain, and in the countries of Europe, resulting in economic and aesthetic losses of staggering proportions. The disease made its appearance in The Netherlands in the year 1919, and was first observed in the United States in 1930. Although tremendous efforts have been made, and vast sums of money expended, in attempting to deal with it, no effective answer has yet been found.

As pointed out in an article from The Chicago Tribune, dated July 31, 1983, more than half a million elm trees have died from Dutch elm disease in the Chicago area in a period of twenty-eight years and across the nation the disease has killed 43 million trees since 1930. This article also points out that efforts to keep the trees from becoming infected have been made by annually injecting trees with an antibeetle chemical, but such efforts are doomed unless trees are quickly uprooted and removed once they are infected, the reason being that elms planted close together often share roots and the common root system enables the disease to move from a diseased tree to a healthy one.

An article in the Manchester Guardian Weekly, Manchester, England, for Aug. 14, 1983, under the heading "Dutch Elm Disease 'Out of Control'", describes the disease as having killed 20 million trees in Great Britain in the past six years. A British official, when asked what is being done to combat the disease, said "Everybody seems to have given up . . . It is getting worse and there is nothing we can do about it." A Forestry Commission spokesman said:

"The tragedy about the disease is that it no longer exists in many parts of southern England because all the trees that were there have either been felled or been killed."

It is therefore apparent that there is a long felt need for a treatment which will counteract Dutch elm disease and preserve elm trees which are fast disappearing from the face of the earth because of this deadly disease.

The disease is caused by the fungus *Ceratocystis ulmi*, which lives and reproduces in the living tissues of the tree, at one stage in its life history vast numbers of infectious spores being produced. The spores speedily germinate and, after a brief period of growth, produce another batch of spores. During these activities the fungus secretes a toxin, which affects the cell walls of the conducting tissues of the tree in such a way that the transport of water and of dissolved nutrients is completely inhibited, so that the tree withers and dies.

The progress of the disease is a direct function of the rate at which the fungus spreads through the tissues of the tree, and the external manifestations are quite variable. Sometimes the leaves at the tips of one or more branches begin to wilt and take on a yellow or brown coloration, and then to drop off; sometimes an entire branch dies and may fall off, while the rest of the tree maintains a healthy appearance continuing in this condition for several seasons, though eventually, once the infection has made its entrance it spreads throughout the tree; sometimes an apparently healthy tree suddenly shows signs of the disease and in the course of a couple of weeks is dead—such a happening showing that, in spite of the healthy appearance, it was already heavily infected, probably in its root system. A twig may be removed from a tree, an extract of its sap made, and a culture of that extract cultivated in a petri dish; tests will then show presence or absence of the fungus. If the test is fungus-positive, that shows that the tree is infected, a result that would almost certainly have been already indicated by the visual appearance of that particular twig; if the test should be fungus-negative, that shows only that the twig selected is free of infection, and tells nothing whatever regarding the condition of the tree as a whole, which may even be heavily infected. Similar considerations hold regarding the presence or absence of the brownish coloration of the water-conducting tissues observable in sections of diseased twigs. Furthermore, microscopic examination of twig or branch sections from diseased trees, even up to 2,500 diameters, discloses no observable difference in the conducting tissues from that of healthy trees. What this amounts to is that, at the present time, the only diagnostic symptoms regarding the condition of a tree are its visual appearance; and in the case of a healthy appearance, that may be quite misleading.

Before a tree can become diseased it is necessary that the infecting spores shall be carried to it, and then should make an entrance into its living tissues. Since the spores are not in any way naturally adapted for transportation by air currents, nor do they possess any appendage capable of piercing the layers of outer bark which protect the tree's delicate conducting tissues, the spread of the infection is totally dependent upon some external agency; and this is provided in two forms: (1) root grafting, and (2) activities of beetles of the genus Scolytus.

(1) if a root of an infected tree should make contact with a root of a healthy one, there is always a possibility that a graft will be established. Should this happen, then at once the infecting spores are in contact with the living tissues of the healthy tree, and the way has been opened for its infection.

(2) the Scolytus beetle lives, feeds and breeds in all kinds of elm material, and should that material happen to be infected, then, when the beetle moves to a new location, it carries the infecting spores with it. Since in its feeding habits the beetle carves an opening through the outer bark of an elm twig or branch to reach the sap-carrying conductive tissue, here again the way has been opened up for infection.

The measures which have been taken in the fight against the disease are either designed to protect healthy trees from infection, or else to cure those already infected and restore them to health. A large number of protective measures have been employed, by far the most important and effective one being termed "Sanitation", the aim being to eliminate possible sources of infection. All infected material is removed and destroyed. Twigs and branches showing signs of infection are removed by pruning and then destroyed. An infected tree is promptly cut down, its stump and roots removed, and all the infected material destroyed. The method is costly, and it is radical in that it involves the loss of the tree.

The spread of the disease by root grafting has been countered by attempting to impregnate the ground near the trees with a solution of sodium N-methyl dithio-carbamate. It is virtually impossible to achieve complete impregnation, and rainfall speedily leaches away the fungicide.

Another protective procedure is the injection of fungicides into the living tissues of healthy trees, and a large number of different fungicides have been used, some rare and costly, some injurious and deadly. The one most frequently chosen at the present time is Arbotect-20 S. When used as directed it may provide a measure of protection, though it is not dependable. Since it is phytotoxic it can be used only in very small amounts and at great dilution, one part to forty or fifty parts of water. For an average size tree this means a relatively costly amount of Arbotect-20 S diluted with water to a volume of 3 gallons. Using gravity feed through an eight-orifice system it takes about eleven days to feed this volume of liquid into the tree. For effective protection the injection should be repeated annually.

A different protective approach is to make the attack upon the beetles, the carriers of the infecting spores. Various ways of doing this have been tried. They can be killed by spraying them with methoxy chlor as they are feeding on the elm trees. But however thoroughly the spraying is done some beetles escape; furthermore it is necessary to spray at least twice each season to correspond with the emergence of the two generations of beetles. The program is expensive. A much less expensive method is to trap the beetles by affixing to the elm trees sticky papers baited with a pheromone; but because of the vast numbers of the beetles this has not proved to be very effective. The wasp Dendrosoter, which destroys the Scolytus larvae, has been used as a biological antagonist; the method is cumbersome, expensive and dangerous, and quite ineffective.

When methods of curing the disease are considered it has to be admitted that practically nothing has been accomplished.

Because the disease known as Dutch elm disease is caused by a specific fungus, one who is unfamiliar and has little knowledge concerning the treatment of such disease could argue that a fungicide which is capable of destroying one type of fungus should obviously be capable of destroying a different type of fungus, but such is not the case. Fungicides are necessarily different, depending upon the type of fungus to be destroyed and also the type of tree to which the fungicide is applied. The mere fact that a fungicidal solution might be injected into a tree provides no answer as to the effect it might have on the particular fungus with which said tree is infected, or whether the injection of the fungicide, while killing a particular fungus, might also be phytotoxic and kill the tree itself. There is also a difference between a fungus which is a deadly fungus and actually kills a tree and a fungus which is not a deadly fungus insofar as the tree is concerned, but affects the foliage or other aspects of the growth of the tree as in the case of fruit bearing trees which are afflicted with scab or powdery mildew. For example, Keil, Agrigultural Chemicals, pages 23,24 and 128, April 1965, claims on page 23, 3rd column, first paragraph, particular successes in controlling Xanthomonas pruni by combinations of dimethyl sulfoxide with other chemical compounds, including organic mercuries, quaternary ammonium compounds, dodine, hexachlorophene, Karathane, zinc sulfate, and oxytetracycline (Terramycin), in spray tests on peach trees to control bacterial spot caused by this microorganism. Using a spraying technique, some protection was obtained for periods of 8-10 days (page 24, first column, last paragraph) on healthy greenhouse plants. After the plants have been infected, the treatment was effective only when carried out within 24 hours of the infection (page 24, second column, paragraph 1). Using an injection technique, two or three injections were made at intervals of two to four weeks, and in the most successful cases 50% reduction in scab infection and 20-30% reduction in powdery mildew infection was obtained within ten feet of the injection point (page 24, column 3, paragraph 2) on Rome Beauty apple trees 25 to 30 years old. It is not clear from this article which chemicals were actually injected into the apple trees but it is apparent to one knowledgeable in this art that these treatments were not effective. A 50% reduction in scab infection could hardly be called an effective treatment and a 20-30% reduction of powdery mildew cannot be called an effective treatment. The article also points out "There also was increased injury with most DMSO combinations. Greatest phytotoxicity usually appeared on the limb immediately above and often to the right of the injector. Orchard trees appeared to withstand 1-2% solutions of DMSO alone without injury, but 10% solutions caused slight leaf-tip burn." While the article is too vague with respect to the specific combinations used so that no one could repeat the tests described by the author, it is clear that the results obtained could not be predicted from one type of fungus to another or from one type of tree to another and the author was not attempting to counteract a deadly disease such as Dutch elm disease which invariably kills the tree. Whatever combinations with dimethylsulfoxide that Keil used in his injections (mostly they are unspecified except in the case of Terramycin), they all caused significant injury to the living trees (page 24, third column, second paragraph).

The Keil article abounds with a large number of speculations (page 128, columns 1 and 2) and admits presumptions and speculations will have to be proved as practical under field conditions and none of these presumptions and speculations are concerned with the problem of counteracting Dutch elm disease.

It should be pointed out to those who are unfamiliar with the art that Hill, U.S. Pat. No. 4,335,109, in order to impart increased water repellancy to cut wood in which the tissues are no longer living, has suggested combining water repellant solutions with a fungicide, reciting vast numbers of fungicides including zinc acetate and zinc sulfate, as well as other zinc compounds in the form of aqueous treating solutions so as to inhibit fungicidal deterioration. The treating solutions are simply deposited on the wood and spread with a sponge. The wood is then dried at ambient temperatures and tested for water repellancy. Nothing in this patent has any relevance to the problem of keeping living tissues alive in trees which are subject to Dutch elm disease. Nor is there any suggestion or teaching in this patent that aqueous solutions of zinc salts in combination with dimethyl sulfoxide would be effective in counteracting Dutch elm disease.

In Herschler, U.S. Pat. No. 3,551,554, human tissue is treated with various physiologically active agents in dimethyl sulfoxide and there is a brief mention that dimethylsulfoxide enhances the penetration of plant active agents such as pesticides, dyes, nutrients, hormones and herbicides, but there is no suggestion or teaching in this patent of any kind of a treatment involving fungicides or of any attempt to solve the problem of counteracting Dutch elm disease.

In view of the long felt need for a solution of this problem and the failure of others to solve it, the present invention becomes particularly important.

BRIEF SUMMARY OF THE INVENTION

Dutch elm disease is counteracted by injecting elm trees susceptible to, or having such disease, with a composition comprising a water soluble zinc salt dissolved in water and mixed with dimethyl sulfoxide in certain predetermined proportions, preferably applied at a time when the sap is returning to the root system. The injection treatment is preferably made into the tree at a depth below the cambium layer and at spaced intervals, the quantity of zinc salt being sufficient to counteract Dutch elm disease, and the quantity of the dimethyl sulfoxide being sufficient to enhance the penetration of the zinc salt.

DETAILED DISCUSSION OF THE INVENTION

In attempting to combat Dutch elm disease, it was first thought that since zinc salts had known fungicidal properties they could be used to treat infected trees. Attempts were made to introduce zinc chloride into the living tissues of trees infected with Dutch elm disease hoping thereby to kill or control the fungus. Zinc chloride paste was sealed into the holes drilled in the trees. Aqueous solutions of zinc chloride were injected under pressure into the trees. After four years of these endeavors the results were both encouraging and disappointing—encouraging because quite frequently slight improvements were apparent in the condition of the trees, but disappointing because the improvements were only superficial and transitory. Often such injections appeared to be helpful giving some temporary amelioration of the symptoms but always the disease came back. It was surmised that this might be due to failure of the solution to reach all parts of the tree and there must be pockets of infection which were always left behind by the treatment. These pockets of infection would then proceed to spread with renewed vigor, eventually killing the tree. This led to a search for a penetrating agent compatible with zinc salts and which, at the same time, would not itself be phytotoxic or kill the tree. It was then conceived that dimethyl sulfoxide might be such a penetrating agent and experiments were carried out on a small tree by injecting massive doses of the zinc salt solution containing dimethyl sulfoxide with results that continued to be beneficial in every way. Laboratory culture tests showed that the solutions used were lethal to the fungus, however, at 250 fold dilution.

Another problem was to make sure that the fungicidal solution was being carried into every part of the root system of the tree for a pocket of infection left there would be fatal. With a deciduous tree such as an elm, this purpose was achieved by making the injection at the time of the year when the sap was descending into the root system but it was also found that this end might be attained, if needful, at some other season by increasing the dosage of the zinc saltdimethyl sulfoxide aqueous solution to more than two fold the normal amount.

Long term observations upon living trees in the field established that this method introduced in effective systemic fashion into the tissues of the tree a composition that is not merely a fungistat but a true fungicide against *Ceratocystis ulmi*.

The best mode contemplated for the practice of the invention comprises dissolving one part by weight of commercially available zinc chloride, sometimes referred to as technical zinc chloride, in one part by weight of water. This will cause the temperature to rise to about 70° C. After cooling to room temperature, one part by weight of technical dimethyl sulfoxide is added and the temperature will rise to about 45° C. No theory is offered regarding the possible formation of chemical compounds or complexes in the process of mixing these constituents.

Using 4 pounds of water, 4 pounds of zinc chloride and 4 pounds of dimethyl sulfoxide, 1 gallon of solution is produced with a specific gravity of 1.44.

Compositions were also prepared in which zinc chloride was replaced by zinc acetate in which case because of the lower solubility of the zinc acetate the formulation for the fungicide solution was 1 part by weight water, 0.53 part by weight zinc acetate dihydrate and 0.40 part by weight dimethyl sulfoxide. Other fungicidal water soluble or water dispersible zinc salts can be used which may be either inorganic or organic. Since the preparation of the composition contemplates dissolving the zinc salt in water, the amount used in such preparation would be limited to the saturation solubility in water at the particular temperature.

The fungicide solution can be injected into the tree by boring holes 1 inch to 1½ inches deep and ¼ inch wide and inserting stainless steel capilliary tubes having an outer diameter of ¼ inch and an inner diameter of 1/16 inch. An alternative is to use T-shaped plastic tubes in which the legs of the T's are inserted into the holes and the cross members are connected by tubing to each other and to a supply of the injecting solutions. The depths to which the tubes are inserted should be sufficient to make contact with the conductive tissue in the tree below the cambium layer.

The amount of fungicide solution injected into the tree is related to the tree size which is measured by the girth of the trunk. Since the root system of the tree is of paramount importance, especially in the treatment of Dutch elm disease, the girth is measured at the point closest to ground level where the trunk proper begins. Numerous experiments with differing amounts of fungicide solution have indicated that an amount of fungicide solution corresponding to one cc per inch of trunk girth gives an effective result and this was the amount used in the tests hereinafter described unless otherwise specified. However, it became evident from experience and in a few cases of heavily infected trees, that the amount of the solution should be increased and better results were obtained by injecting 5 cc of solution per inch of trunk girth. For an average size tree having a girth of six feet, this requires the injection of 360 cc of solution. Since the chemicals involved are relatively inexpensive, the costs are quite low.

The invention will be further illustrated but is not limited by the following examples.

EXAMPLE I

A large widely branched elm having a girth of 7 feet was markedly infected with Dutch elm disease. A fungicide solution composed of equal parts by weight of water, zinc chloride and dimethyl sulfoxide prepared by first adding the zinc chloride to the water and then adding the dimethyl sulfoxide in the manner previously described, was injected into the tree through a stainless steel capilliary tube having an outer diameter of ¼ inch and an inner diameter of 1/16 inch driven into the trunk deeply enough to make contact with the conductive tissues at a pressure of 30 psig supplied from a cylinder of carbon dioxide applied to the solution. 50 cc were injected. Eighteen years later the tree appeared to be fine and healthy.

EXAMPLE II

To test the phytotoxicity of the solution a small healthy appearing young elm was selected having a girth of 14 inches. A massive dose of 900 cc of a fungicide solution of type described in Example I was injected at a pressure of 25 psig. This dose amounts to over 64 cc per inch of girth. The tree never showed the least sign of injury and has continued to grow and flourish though surrounded by elm trees that have died from Dutch elm disease. It has been given no further attention and 14 years later appeared to be fine and healthy.

EXAMPLE III

Two young elm trees each showing marked signs of infection were each injected with 25 cc of fungicide solution of the type described in Example I, and in the manner described in Example I, at 25 psig pressure. Thirteen years later both trees appeared to be in fine shape.

EXAMPLE IV

An elm tree badly infected with Dutch elm disease, having a girth of 4 feet 2 inches was injected with 50 cc of the fungicide solution described in Example I in the Fall of the year at a time when the sap was being withdrawn into the root system and without applying any pressure in the injection of the fungicide solution. Consequently, the fungicide solution was driven into the root system also, there to remain throughout the dormant season during which time the roots will be purged of all infection. In the springtime the ascending sap will carry the fungicide into every other part of the tree. This tree made a phenomenal recovery and has continued to thrive without any further attention, although surrounded by dead and dying elms in close proximity. Seven years later the tree appears to be in perfect health.

EXAMPLE V

In October two small elms, both apparently healthy, were each injected with 75 cc of the fungicide solution described in Example I without any pressure. These trees have remained healthy and in August, six years later, appeared to be in good shape.

EXAMPLE VI

In October, an elm tree having a girth of 3 feet, very definitely infected with Dutch elm disease, was injected with 10 cc of a zinc acetate solution prepared as previously described without pressure. In August, six years later, the tree was in good condition.

EXAMPLE VII

In October, 2 small elms with marked signs of Dutch elm disease, one having a girth of 2 feet and the other having a girth of 2 feet 2 inches were each given 10 cc of a solution as prepared in Example I. In August, six years later, both trees were apparently in good condition.

EXAMPLE VIII

In June, an elm tree badly infected with Dutch elm disease, having a girth of six feet was given an injection of a solution as described in Example I in an amount of 8 cc per inch of girth or a total of 400 cc of fungicide solution. In August, three years later, the tree was in fine shape.

In the following examples the injection of the fungicide solution into the trees was carried out using an arrangement of gravity feed through a series of T-shaped plastic feed tubes connected with rubber tubing and arranged at 8 inch intervals around the tree. In this way, regardless of the girth of the tree, the injection of the fungicide, one cc per inch, was accomplished in about the same length of time, namely 6–15 minutes.

EXAMPLE IX

An elm tree badly infected with Dutch elm disease having a girth of 3 feet 4 inches, was injected with 300 cc of the fungicide solution described in Example I. In June, a year later, the tree was apparently recovering but was cut down.

EXAMPLE X

An elm tree badly stricken with Dutch elm disease having a girth of 3 feet was injected with 40 cc of the fungicide solution described in Example I in June. In April of the following year the tree was dead, indicating that the amount of the fungicide treating solution was insufficient.

EXAMPLE XI

In October, two elm trees, one having a girth of 10 feet 5 inches, definitely infected with Dutch elm disease, was treated with 125 cc of a fungicide solution of the type described in Example I, and the second having a girth of 7 feet severely stricken with Dutch elm disease, was treated with 85 cc of fungicide solution of Example I. In August, three years later, both trees were in perfect shape.

EXAMPLE XII

In July, two elm trees both severely stricken with Dutch elm disease, one having a girth of 2 feet 2 inches, was treated with 270 cc of the fungicide solution of Example I, and the other having a girth of 2 feet 7 inches was treated with 300 cc of the fungicide solution of Example I. In August, two years later, both trees were fine and healthy.

In the course of the testing program 17 severely stricken trees of which three appeared to be at the point of death, were restored to apparent health. Twenty definitely infected trees were restored to perfect health. Of 28 trees which originally appeared to be healthy——and this does not mean that they were healthy, only one was lost by death, and at the conclusion of the program four showed signs of infection. Ten trees without further attention after the original treatment remained resistant to infection for periods from 4–18 years.

Based on the test results obtained, the preferred method of treatment is to inject the fungicide solution at a dosage of 5 cc per inch of trunk girth at a time when the sap is being withdrawn into the root system. This injection can be made as already described or in any other suitable manner, for example, from an aerosol container containing the fungicidal solution and a suitable propellant.

Dimethyl sulfoxide is a well known chemical compound described in the Merck Index, 7th Ed., page 373, as being a very hygroscopic liquid with practically no odor or color, soluble in water, ethanol, acetone, ether, benzene and chloroform. It has been used as a solvent for acetylene, sulfur dioxide and other gases, as an antifreeze or hydraulic fluid when mixed with water, as a solvent for some organic compounds, as a paint and varnish remover, and as a solvent for some hydrocarbons.

The quantity of dimethyl sulfoxide used in the practice of the invention is sufficient to enhance the penetration of the zinc salt into the living tissues of the tree but such that the zinc salt is not precipitated from its solution in water.

The advantages of the invention are manifested in that it is now possible to counteract and control Dutch elm disease by a simple injection method using chemicals that are relatively inexpensive and which are not phytotoxic to elm trees. When methods heretofore used or attempted to be used for curing th disease are considered, it has to be admitted that practically nothing has been accomplished. Very cautious claims are sometimes made for the treatment of elm trees if the tree is less than 5% infected, though no information is ever given relative to the determination of that 5% degree of infection, but there does seem to be universal agreement that, cases where there is a marked degree of infection, the tree is doomed. Recently a curative approach has been described which uses an antimycotic agent to attack *Ceratocystis ulmi*. Tests made on lightly infected trees indicate limited success. However, the present invention as shown by the examples provides in one injection 100% effectiveness and control over a period of years, irrespective of whether the tree was either healthy or already infected.

It should also be noted that whatever combinations with dimethyl sulfoxide Keil used in his injections (mostly they are unspecified except in the case of Terramycin) they were all quite different from the compositions employed in the practice of the present invention because they caused significant injury to the living trees. As for the treatment of cut wood, that is to say, wood in which the tissues are no longer living and the sap is no longer flowing, for the purpose of fungicidal protection against fungi which are quite different from the fungus causing Dutch elm disease, there is in fact no relationship and no valid comparisons can be made.

The invention is hereby claimed as follows:

1. A process for counteracting Dutch elm disease in living elm trees which are susceptible to said disease which comprises injecting into the trunk of the tree beneath the cambium layer a quantity of a solution which is non-pytotoxic to elm trees and consists essentially of a solution of one part by weight of a zinc salt in the form of zinc chloride dissolved in one part by weight of water and mixed with one part by weight of dimethyl sulfoxide, the quantity of said solution being at least 5 cc per inch of trunk girth and being sufficient to counteract Dutch elm disease and the quantity of dimethyl sulfoxide being sufficient to enhance the penetration of said solution in the living tissues of the tree, and the composition being such that the zinc chloride is not precipitated from its solution in water.

2. A process as claimed in claim 1 in which injection of said composition into the tree is at a time when sap is being withdrawn into a root system of the tree.

3. A process for counteracting Dutch elm disease in living elm trees which are susceptible to said disease which comprises injecting into the trunk of the tree beneath the cambium layer a quantity of a solution which is non-phytotoxic to elm trees and consists essentially of a solution of 0.53 part by weight of zinc acetate dihydrate salt dissolved in one part by weight of water and mixed with 0.4 part by weight of dimethyl sulfoxide, the quantity of said solution being at least 5 cc per inch of trunk girth and being sufficient to counteract Dutch elm disease and the quantity of dimethyl sulfoxide being sufficient to enhance the penetration of said solution in the living tissues of the tree and the composition being such that the zinc acetate is not precipitated from its solution in water.

4. A process as claimed in claim 3 in which injection of said composition into the tree is at a time when sap is being withdrawn into a root system of the tree.

5. A composition for counteracting Dutch elm disease in living elm trees which are susceptible to said disease which consists essentially of a non-phytotoxic solution obtainable by dissolving in one part by weight of water one part by weight of zinc chloride salt and mixing therewith one part by weight of dimethylsulfoxide, the amount of said zinc chloride salt and said dimethylsulfoxide being such that the zinc chloride salt is not precipitated from the resulting solution.

6. A composition for counteracting Dutch elm disease in living elm trees which are susceptible to said disease, said composition consisting essentially of a non-phytotoxic solution obtainable by dissolving in one part by weight of water, 0.53 part by weight of zinc acetate dihydrate salt and 0.4 part by weight of dimethylsulfoxide, the amount of said zinc acetate salt and said dimethylsulfoxide being such that the zinc acetate salt is not precipitated from the resulting solution.

* * * * *